United States Patent [19]

Rowell, Sr.

[11] Patent Number: 4,827,920
[45] Date of Patent: May 9, 1989

[54] RESTRAINT SYSTEM

[76] Inventor: Richard H. Rowell, Sr., Rte. 2, Box 340 E, Waycross, Ga. 31501

[21] Appl. No.: 2,944

[22] Filed: Jan. 13, 1987

[51] Int. Cl.$^4$ ............................................. A61F 13/00
[52] U.S. Cl. ................................... 128/875; 297/465
[58] Field of Search ............... 128/133, 134, 75, 78; 297/464, 465; 182/3, 4

[56] References Cited

U.S. PATENT DOCUMENTS

| | | | |
|---|---|---|---|
| 2,450,162 | 9/1948 | Promen | 128/134 X |
| 3,042,031 | 7/1962 | Reed | 128/134 |
| 3,247,843 | 4/1966 | Callahan | 128/134 |
| 3,742,945 | 7/1973 | Reinhardt | 128/134 |
| 3,788,309 | 1/1974 | Zeilman | 128/134 |
| 4,141,368 | 2/1979 | Meyer | 128/134 |
| 4,205,670 | 6/1980 | Owens | 128/134 |
| 4,434,793 | 3/1984 | Willits | 128/134 |
| 4,536,903 | 8/1985 | Parker | 128/134 |

Primary Examiner—Richard J. Apley
Assistant Examiner—J. Welsh
Attorney, Agent, or Firm—Michael C. Smith

[57] ABSTRACT

A restraint system for use in maintaining a patient on a patient supporting structure comprising, a harness adapted to fit on the torso of the patient, a flexible strap assembly connected to said harness, said strap assembly having a plurality of openings therethrough at spaced apart positions axially of said strap assembly, a flexible connector adapted to selectively extend through any selected of said openings in said strap assembly, and an attachment for connecting said flexible connector to the patient supporting structure.

9 Claims, 6 Drawing Sheets

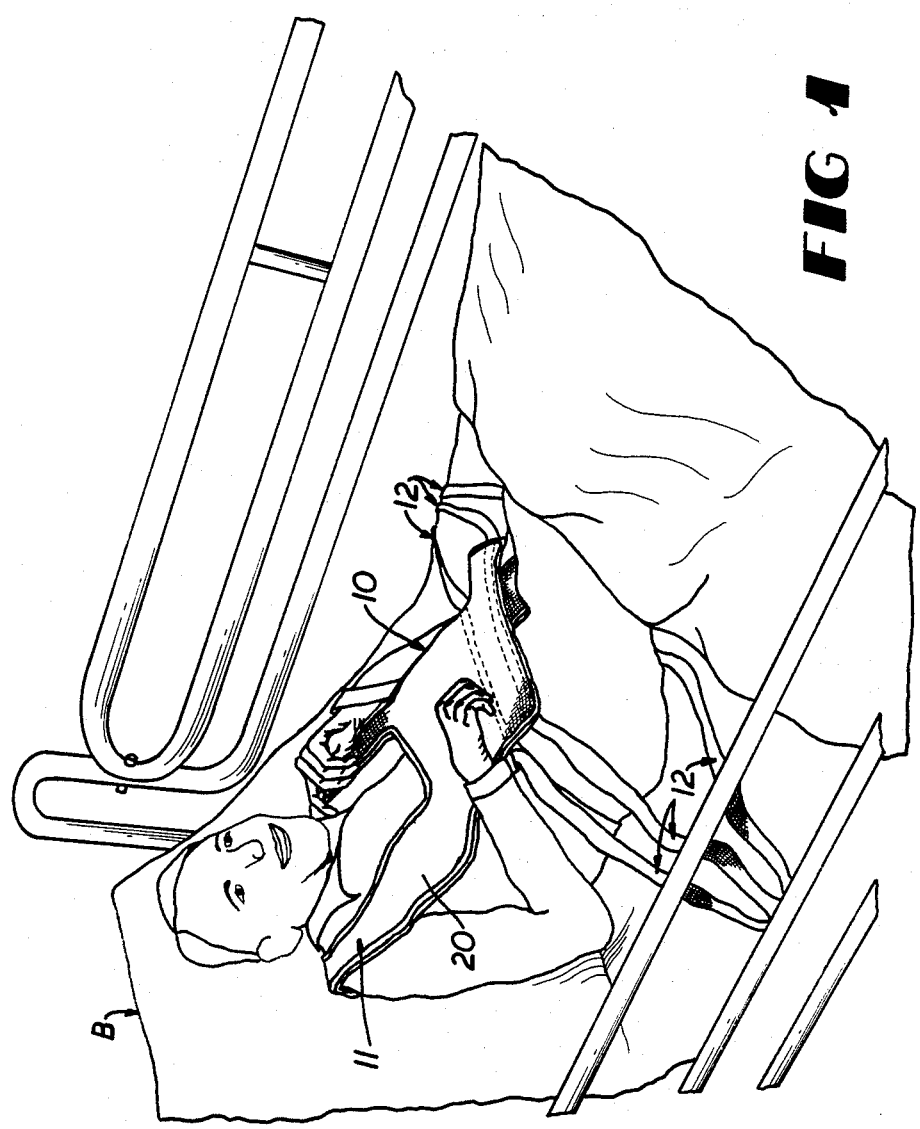

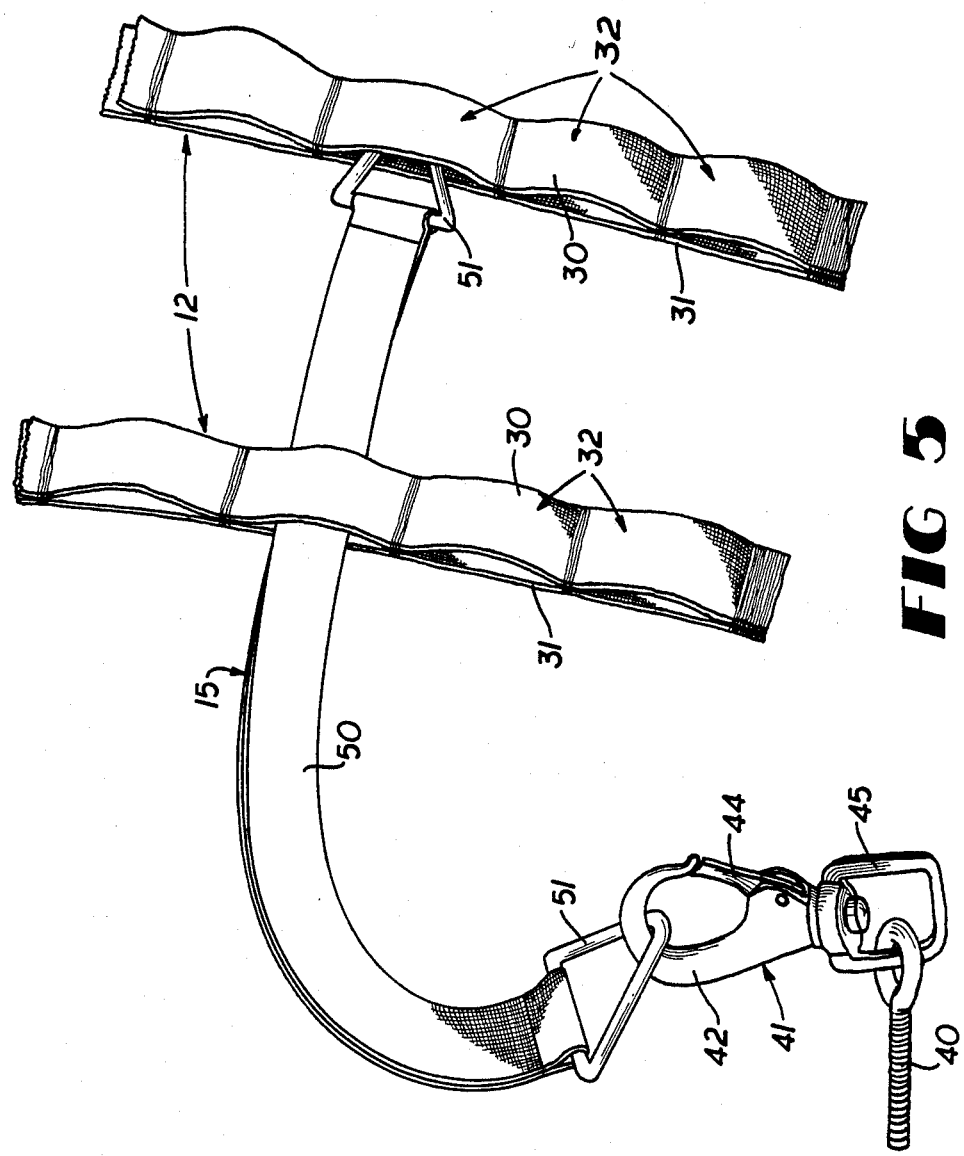

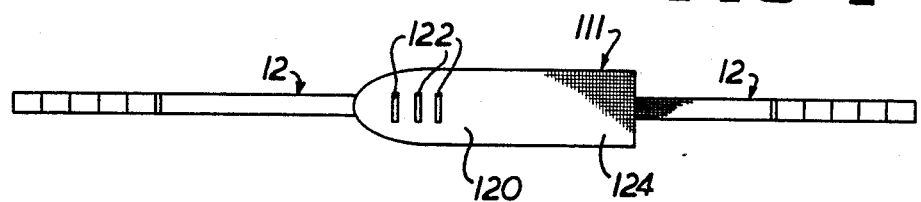
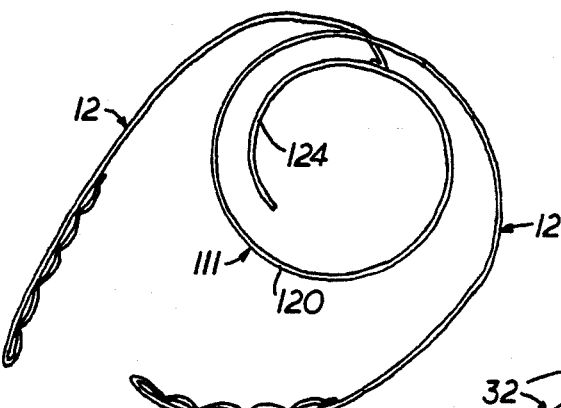
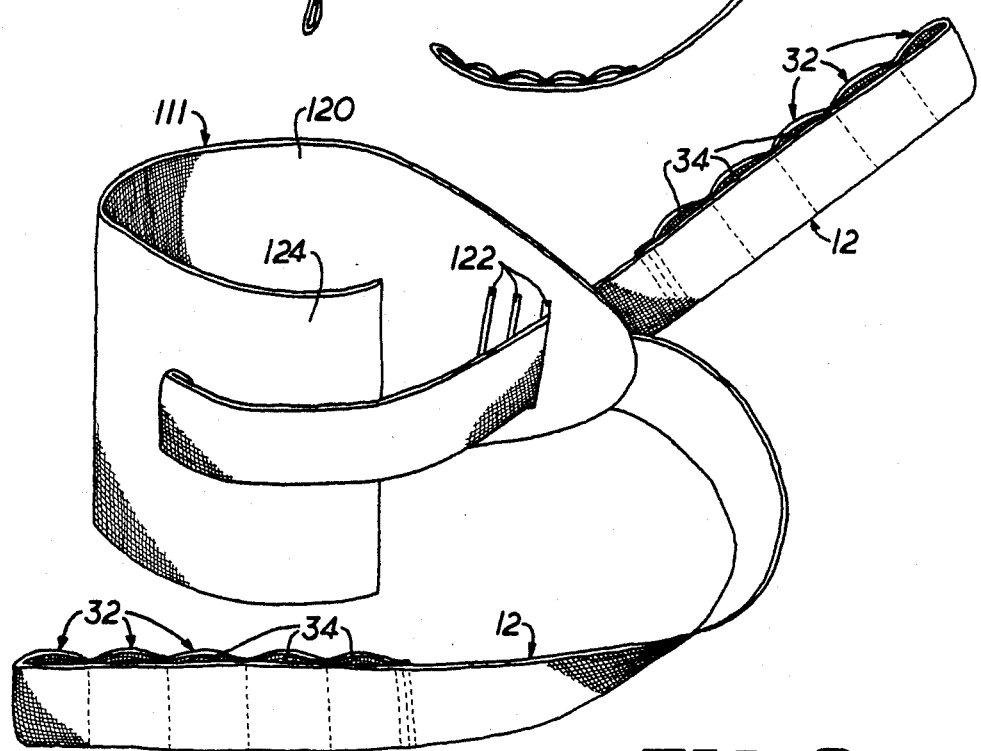

RESTRAINT SYSTEM

BACKGROUND OF THE INVENTION

This invention relates generally to restraining devices and more particularly to a restraint system used to restrain and protect patients in beds, wheelchairs, and other support structures.

Restraining devices to help keep patients on supporting structures such as beds, wheelchairs, straight chairs, transport tables and the like are presently available. Various arrangements have been suggested as disclosed in the following prior art patents:

| Patent No. | Issue Date | Inventor | Class/Subclass |
|---|---|---|---|
| 2,848,993 | Aug. 1958 | Terrell | 128/134 |
| 2,912,977 | Nov. 1959 | Holbrook | 128/134 |
| 3,788,309 | Jan. 1974 | Zealman | 128/134 |
| 3,878,844 | Apr. 1975 | Tobias | 128/134 |
| 3,897,778 | Aug. 1975 | Forbes-Robinson | 128/134 |

One of the problems with these prior art restraints is that they have been difficult to secure to the supporting structure so that the patient was unable to disconnect the restraint. Another problem with most of these prior art restraints is that there is no mechanism through which the restraint can be rapidly disconnected from the supporting structure in order that the patient can be removed from the structure in case of an emergency.

SUMMARY OF THE INVENTION

These and other problems and disadvantages associated with the prior art are overcome by the invention disclosed herein by providing a restraint system which will maintain the patient on the supporting structure in which the patient is located while isolating the connection points of the restraint to the supporting structure from the patient, which permits the maximum freedom of movement of the patient while being restrained on the supporting structure in case of an emergency. The restraint system of the invention can be applied to various types of harnesses used to connect the restraint system to the patient and also to various types of support structures.

The restraint system incorporating the invention includes a harness structure which is fitted to the patient; a plurality of flexible strap assemblies connected to the harness structure, each of the flexible strap assemblies including a plurality of loops placed at different positions lengthwise of the strap; an attachment connecting structure mounted on the patient supporting structure; and a flexible connector removably receivable through one of the loops on each of the flexible straps connected to the harness structure to connect the harness structure to the patient's supporting structure when the flexible connector is extended through the loops and attached to the attachment connecting structure. The restraint system can be universally used on different patient supporting structures such as beds, wheelchairs, operating trolleys and the like.

These and other features and advantages of the invention will become more fully understood upon consideration of the following detailed description and accompanying drawings wherein like characters of reference designate corresponding parts throughout the several views and in which:

BRIEF DESCRIPTION OF THE DRAWINGS

FIG. 1 is a perspective view illustrating the invention in use;

FIG. 5 is a perspective view illustrating the connection of the flexible straps to the flexible connector;

FIG. 7 is a face view of the invention applied to an alternate harness structure;

FIG. 8 is a perspective view of the invention of FIG. 7 being readied for use; and FIG. 9 is an edge view of the invention of FIG. 7 being readied for use.

Figure 4:
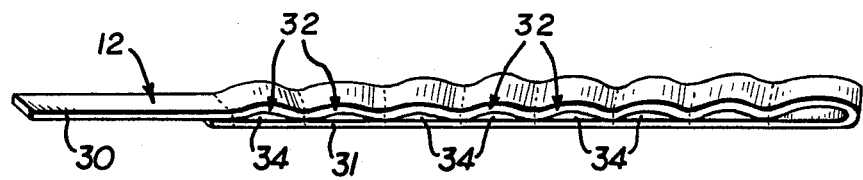
FIG. 4 is an enlarged side elevational view of one of the flexible strap assemblies showing the loop structure.

These figures and the following detailed description disclose specific embodiments of the invention; however, it is to be understood that the inventive concept is not limited thereto since it may be embodied in other forms.

DETAILED DESCRIPTION OF ILLUSTRATIVE EMBODIMENTS

Referring to the figures, it will be seen that the restraint system 10 includes a harness 11 which is to be worn by the patient, a plurality of flexible strap assemblies 12 connected to the harness 11, an attachment connecting assembly 14 mounted on the patient supporting structure such as the bed B and flexible connectors 15 to connect the flexible strap assemblies 12 to the attachment connecting assembly 14.

Figure 3:
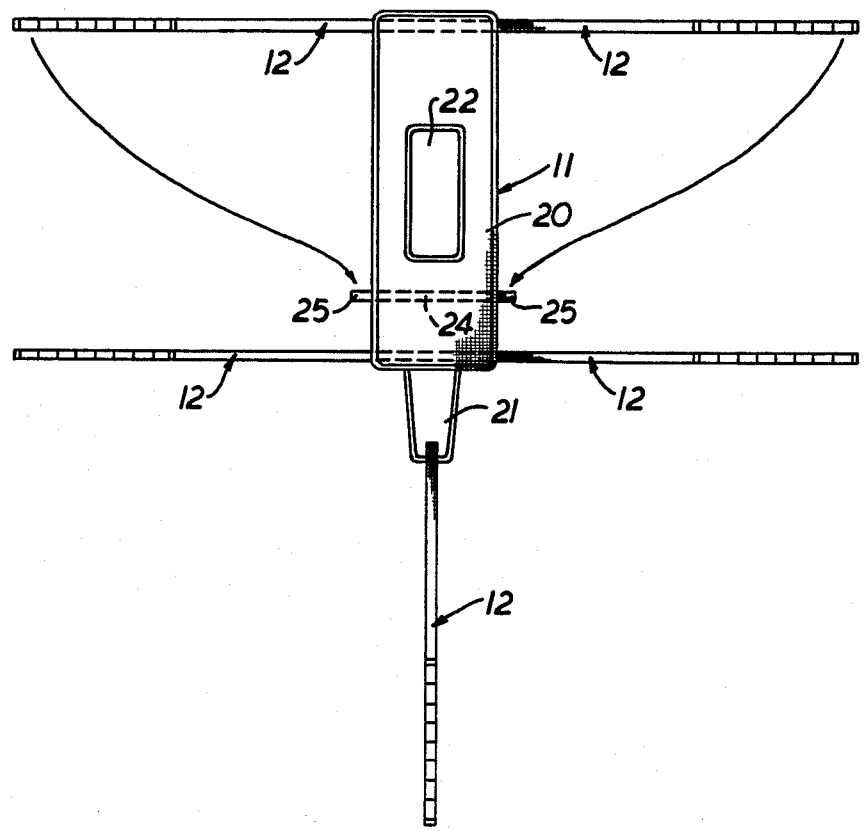
FIG. 3 is a top plan view illustrating the harness and flexible strap structure of one embodiment of the invention.

While it will be understood that different harnesses may be used, the harness 11 illustrated in FIG. 3 is made out of fabric and includes generally a rectilinear main panel 20 with a crotch panel 21 connected to one end thereof. This particular configuration is common in the industry. The main panel 20 has a central cutout 22 so that it will fit over the head of the patient. A strap retainer 24 extends across the main panel 20 between the cutout 22 and the crotch panel 21 to provide strap loops 25 on opposite sides of the main panel 20 as will become more apparent.

A pair of the flexible strap assemblies 12 are connected to each end of the main panel 20 and project outwardly therefrom. A pair of strap assemblies 12 are also connected to the projecting end of the crotch panel 21. These flexible strap assemblies 12 are connected to the crotch panel 21 at a common location.

Each of the flexible strap assemblies 12 includes main strap 30 which is connected to the main panel 20 or crotch panel 21 and projects outwardly therefrom. While the straps 30 may have different lengths, depending on the specific application, it has been found that a length of about 2-4 feet will typically suffice. The projecting end of each strap 30 is provided with a loop forming member 31 that extends along the strap 30 back toward the harness 11. The member 31 is sewn to the strap 30 at spaced apart positions lengthwise of the strap 30 to form loops 32 with the strap 30. The passage 34 through each of the loops 32 has a size to slidably receive the flexible connector 15 therethrough as seen in FIG. 5. While this size may vary with different size connectors 15, it has been found that sewing the member 31 to the strap 30 on 2-3 inch centers is ususally satisfactory. Typically the straps 30 on opposite sides of the main panel 20 are made as one piece and extend across the main panel 20 to be sewn thereto.

Figure 2:
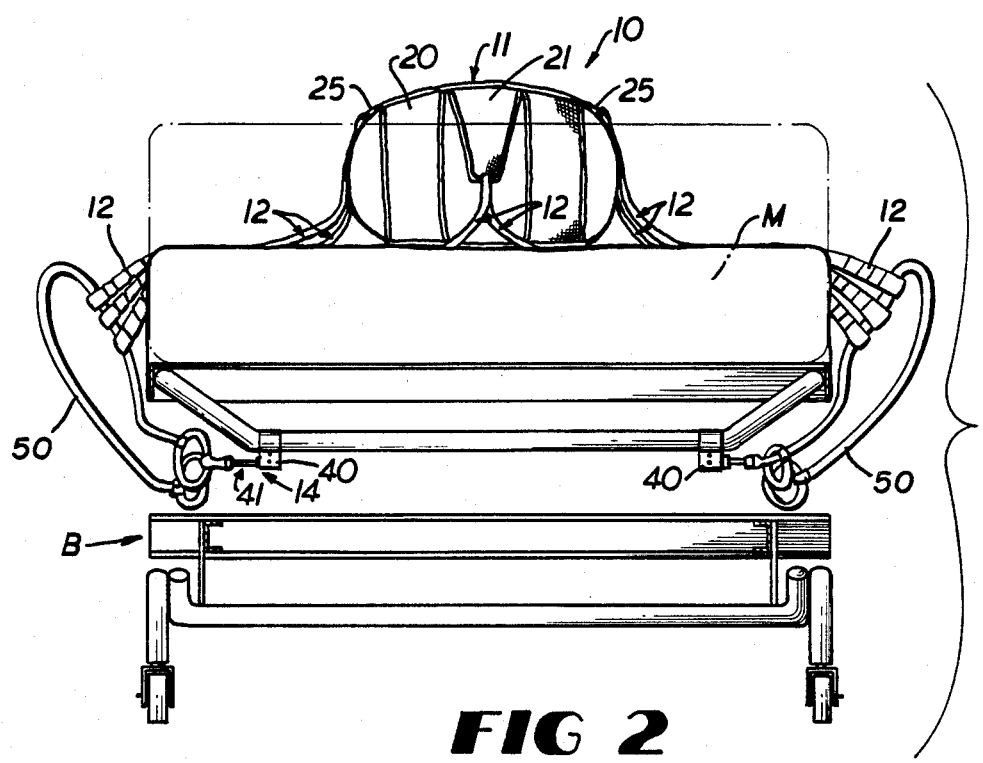
FIG. 2 is a transverse cross-sectional view of the patient supporting structure showing the invention in use.

Each attachment connecting assembly 14 best seen in FIGS. 2 and 5 includes an eye bolt 40 adapted to be connected to the patient support structure. On the bed B as seen in FIG. 2, the eye bolt 40 is connected to the cross tube CT that moves with the upper portion of the mattress M as it is adjusted. This keeps the eye bolts 40 on opposite sides of the bed B out of reach of the patient while at the same time maintaining the same spacing between the patient's upper torso and the eye bolts as the bed is adjusted. A swivel hook assembly 41 is mounted in the eye of each bolt 40. The assembly 41 has a hook 42 equipped with a spring loaded retainer 44 and a swivel 45. The eye on bolt 40 is mounted through the swivel 45 so that the hook 42 can shift around eye bolt 40 and swivel in swivel 45 to keep the line of force extending axially through hook 42.

Figure 6:
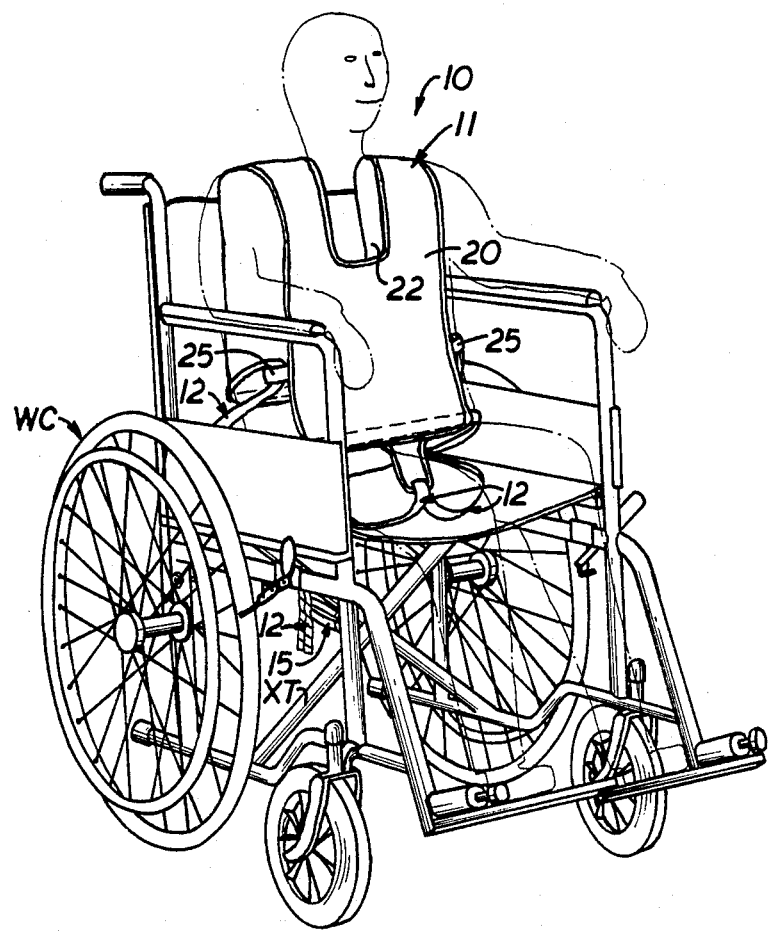
FIG. 6 is a perspective view illustrating the invention used in connection with a wheelchair.

Each flexible connector 15 includes an elongate flexible connector member 50 provided at opposite ends thereof with connector rings 51 defining connector openings 52 therethrough sized to receive the hook 42. The connector member 50 has a length sufficient to extend through the desired number of strap assemblies 12, three are illustrated in FIGS. 1, 2 and 6, and to the hook assembly 41 with which it will be used. One typical length is about one foot. The connector member 50 may be made out of any flexible material of the appropriate strength. The member 50 illustrated is made out of a webbing material. Likewise any convenient connector rings 51 may be used. The rings 51 illustrated are triangular shaped and made of teal rod. The rings 51 may be eliminated and the openings 52 made in the ends of connector member 50.

In use, the harness 11 seen in FIG. 3 is placed over the patient's head so that one set of strap assemblies 12 are located behind the person while the other set is located in front of the person. The set of strap assemblies 12 opposite strap loops 25 are passed through these loops so that these back strap assemblies 12 are located parallel to the front strap assemblies 12 and both are located at about the patient's waist. The crotch strap assemblies 12 are passed under the patient's legs and are also located in the same general position as the other strap assemblies at this point.

When the patient is in bed B as seen in FIGS. 1 and 2, one of the flexible connectors 15 is used to extend through the appropriate loops 32 in the three strap assemblies 12 on one side of the patient and another connector 15 used on the opposite side. After the connectors 15 extend through the strap assemblies 12, they are connected to the appropriate hook assembly 41 as seen in FIG. 2.

When the wheelchair WC is to be used, one of the attachment connecting assemblies 14 is connected to the pivot between the X-tubes, XT on the wheelchair as seen in FIG. 6. One or two of the flexible connectors 15 can be used to attach the strap assemblies 12 to the hook assembly 41.

FIGS. 7-9 disclose an alternate embodiment of the harness which has been designated 111. The harness 111 can be made in different sizes to be used on a patient's waist, thigh, ankle or arm. Harness 111 includes a fabric elongate main panel 120 defining a plurality of slots 122 therethrough adjacent one end and spaced apart axially of th panel. The strap assemblies 12 are attached to opposite ends of the panel 120 so that the strap assembly 12 opposite slots 122 can pass through a selected one of the slots to provide for size adjustment. The assembly 12 for passage through slots 122 is attached to the panel 120 inboard of its end to provide an over flap 124 for comfort. The panel 120 limits the passage of strap assembly 12 through slots 122 to prevent too much restriction being applied to the patient.

I claim:

1. A restraint system for use in maintaining a patient on a patient supporting structure comprising:
    (a) a harness adapted to fit on the torso of the patient, said harness having a rectilinear main panel; a central aperture through which the head of said patient extends; a crotch panel secured to a forward end of said main panel; a pair of flexible strap assemblies connected to each of said main panel and projecting outwardly therefrom; a pair of strap assemblies secured at a common location to a projecting end of said crotch panel; further provided that each flexible strap assembly has a plurality of spaced apart openings axially therethrough;
    (b) an elongated flexible connector, adapted to pass through any of said openings; said elongated flexible connector having an elongated member of webbing material with a connector ring secured to each end thereof; and
    (c) attachment means for securing each of said connector rings to said patient supporting structure.

2. The restraint system of claim 1 wherein each of said flexible strap assemblies includes a main strap connected to said harness and a loop forming member sewn to said main strap at spaced apart positions to form said openings.

3. The apparatus of claim 1 comprising a strap retainer extending across said main panel between said central aperture and said crotch panel, with a plurality of strap loops formed on each side thereof.

4. The apparatus of claim 1 wherein said harness is constructed of flexible fabric.

5. The apparatus of claim 1 wherein each of said flexible strap assemblies has a length of from about 2 feet to about 4 feet.

6. The apparatus of claim 1 wherein each flexible strap assembly comprises an elongated strap and an elongated loop forming member secured to said strap at a multiplicity of positions along said strap from about two inches to about three inches apart, forming said axial openings therebetween.

7. The apparatus of claim 1 wherein flexible straps assemblies on opposite sides of said harness are formed of a single continuous strap.

8. The apparatus of claim 1 wherein each attachment means comprises an eye bolt, a swivel hook mounted in the eye of said eye bolt, and a spring loaded retainer for releasably enclosing the opening of said hook.

9. The apparatus of claim 1 wherein said elongated flexible connector is about one foot in length.

* * * * *